United States Patent
Atad et al.

[11] Patent Number: 6,135,989
[45] Date of Patent: *Oct. 24, 2000

[54] PRESSURIZED INTRAVENOUS INFUSION BAG

[76] Inventors: Jack Atad, 34, Lascov Street, Haifa 34050; Zeev Goldik, 48, Hantke Street, Haifa 34608; Barry Plotkin, 32, Hanarkisim Street, Kiryat-Bialik 27214, all of Israel

[ * ] Notice: This patent issued on a continued prosecution application filed under 37 CFR 1.53(d), and is subject to the twenty year patent term provisions of 35 U.S.C. 154(a)(2).

[21] Appl. No.: 09/078,282

[22] Filed: May 13, 1998

[30] Foreign Application Priority Data

Mar. 26, 1998 [IL] Israel ......................................... 123839

[51] Int. Cl.⁷ .................................................. A61M 37/00
[52] U.S. Cl. ........................................... 604/410; 604/408
[58] Field of Search ..................... 604/408, 409, 604/410, 415, 416, 8, 9; 206/219, 222, 419, 420; 383/901, 38

[56] References Cited

U.S. PATENT DOCUMENTS

| | | |
|---|---|---|
| Re. 27,132 | 6/1971 | Ilg . |
| 2,387,598 | 10/1945 | Mercier . |
| 2,595,493 | 5/1952 | Slaby et al. . |
| 2,766,907 | 10/1956 | Wallace, Jr. . |
| 4,396,382 | 8/1983 | Goldhaber ................................ 604/28 |
| 5,207,638 | 5/1993 | Choski et al. .............................. 604/4 |
| 5,257,985 | 11/1993 | Puhl ........................................ 604/408 |
| 5,505,708 | 4/1996 | Atkinson . |
| 5,693,040 | 12/1997 | Prior ....................................... 604/410 |
| 5,792,133 | 8/1998 | Rochat .................................... 604/406 |
| 5,810,202 | 9/1998 | Hoback et al. . |

*Primary Examiner*—Mark O. Polutta
*Assistant Examiner*—David J. Cho
*Attorney, Agent, or Firm*—Frishauf, Holtz, Goodman, Langer & Chick, P.C.

[57] ABSTRACT

A intravenous infusion device which includes a bag of an impervious flexible material which is divided into two compartments by a central partition of an impervious flexible material. A first compartment is filled with an infusion liquid and contains an outlet provided with a connection to a flexible hose and an infusion needle. The second compartment is empty and has an inlet provided with a connector to an inflation device such as a hand-operated balloon. This second compartment can be inflated to exert a pressure on the first compartment in order to cause the infusion liquid to be conveyed into the patient's vein at the required rate of flow. The infusion device can be used in all cases where the bag cannot be suspended above the patient as for instance on the battlefield or after an accident. It is likewise suitable in all cases where an increased rate of infusion is required.

12 Claims, 3 Drawing Sheets

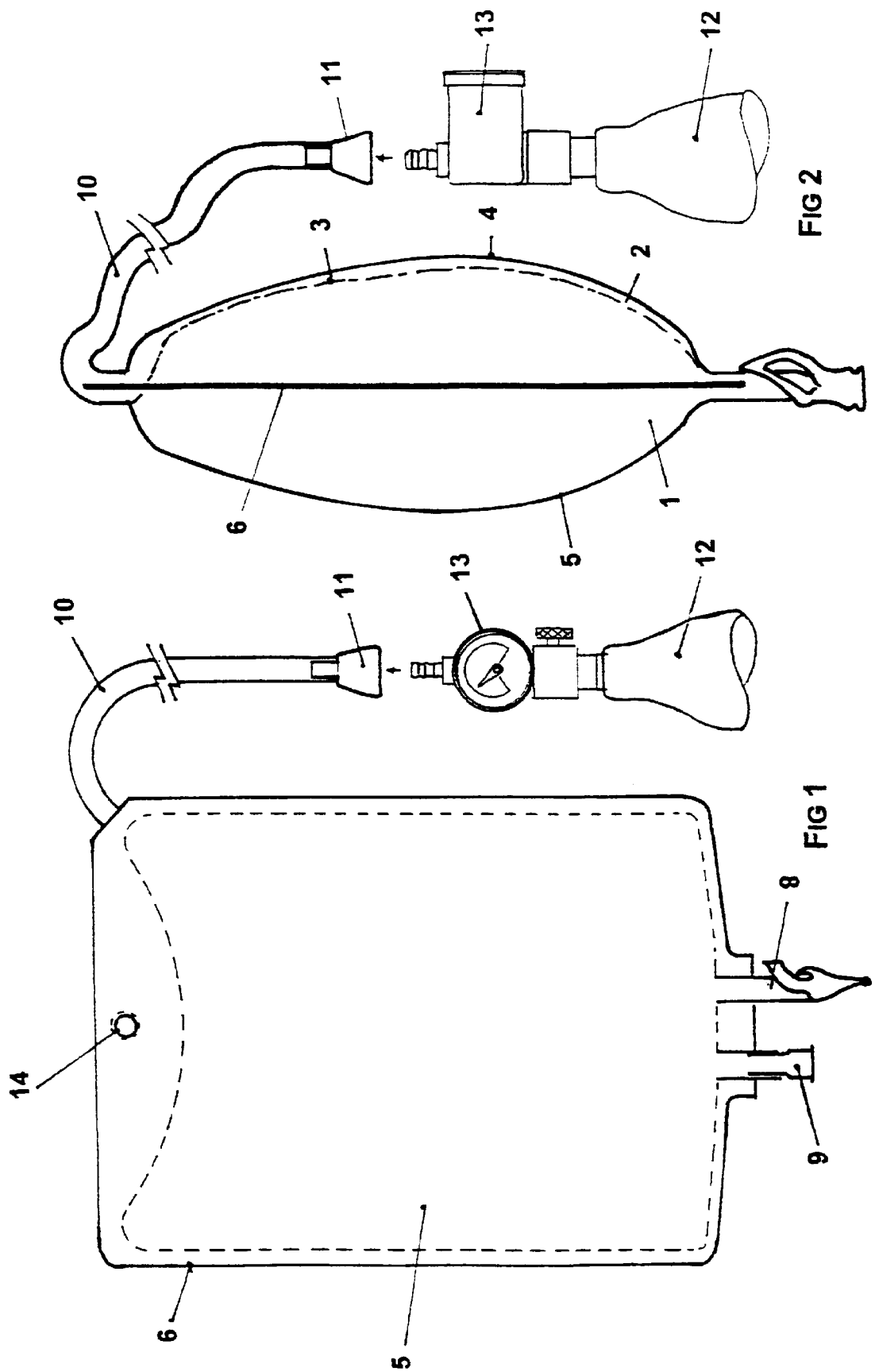

PRESSURIZED INTRAVENOUS INFUSION BAG

The invention relates to an infusion device which is to be used in emergency cases and in all cases where rapid infusion into a vein of a patient is required. It relates particularly to a bag of an impervious plastic material filled with a medicinal solution or blood to be infused into a patient by means of a flexible tube and an intravenous needle.

Another use of the infusion device is related to endoscopic procedures where infusions of different liquids are introduced under pressure into different organs such as to the uterus (Hysteroscopy), urinary bladder (Cystoscopy) and into various articulations (Atheroscopy).

BACKGROUND OF THE DISCLOSURE

Intravenous infusion solutions are supplied in standard plastic disposable bags. They are conventionally suspended from a hook on a stand and the infusion liquid is delivered into the vein or the marrow of the bone by an injection or trocar needle. In situations where no stand or other raised object is available for suspending the bag, this last one must be held above the patient by a nurse or paramedics in order to ensure liquid flow by gravity, evidently occupying the person unnecessarily, while he or she could treat other patients in the meantime.

In order to remedy this drawback, several devices have been developed which are designed to hold a conventional infusion bag and to impose a certain pressure onto its side walls so as to cause the liquid to flow out through the needle into the patient's blood stream. A first device includes two flexible boards which are hingedly connected at one end and interconnected at the other as soon as a bag has been placed between the two boards. This device suffers from the drawback of exerting initial high pressure on the bag which pressure gradually diminishes towards the end of the infusion process. Another device includes two spaced-apart inflatable bags to be placed applied to the two side walls of the infusion bag. By gradually inflating those bags it will be possible to attain an even pressure onto the infusion bag resulting in an even flow of infusion. Still another device contains a solid support opposite one inflatable bag, adapted to have the infusion bag to be placed between board and inflatable bag.

All three devices have to be held in stock in addition to the regular infusion bags, or have to be carried separately to the place of an accident, or into the battle field and must be operated as separate units.

It is, therefore, the main object of the present invention to provide an infusion bag which includes integral means for causing an even flow of infusion liquid, irrespective of the relative position of the bag with regard to the patient, e.g., the device can be placed on the floor or on the stretcher of the patient.

It is another object of the invention to provide an infusion bag to be operated without the above-mentioned drawbacks.

Still another object is to provide an infusion bag of almost the same size and weight as the conventional bag, but with the inherent means for causing regular liquid flow.

Furthermore it is a final object to provide the bag of the present invention at a cost not much higher than the cost of a conventional infusion bag.

SUMMARY OF THE INVENTION

A preferred embodiment of the infusion device according to the present invention includes a bag of an impervious and flexible material which is divided into two adjoining compartments by a partition of the same or an equivalent impervious and flexible material. A first compartment is provided with an outlet port and connection means for attachment of a flexible tube, a flow controller, an injection needle and a drop-counting device. It is furthermore provided with a separate connection for introducing supplementary medical solutions into the bag. The compartment is completely filled with an infusion liquid; it is then sealed and sterilized until the device is to be used. The second compartment is provided with connecting means to an inflating device, e.g., a balloon pump with a check valve, as well as a pressure gauge. After the first compartment has been connected to the vein of a patient by means of needle and tube the second compartment is inflated by means of the pump until the required flow rate is attained. With continued emptying of the first compartment the pressure in the second compartment is gradually increased in order to maintain the liquid flow. The device may also serve to initially provide a much greater liquid flow rate than generally caused by suspension and gravity, a matter important in many accident situations.

Instead of inflation by a hand-operated pump it is also feasible to provide the infusion device with self-inflating means as known to the art. As an alternative it may be connected to a compressed gas cylinder provided with pressure controls.

A second embodiment of the infusion device includes two bags of identical outer dimensions, both made of an impervious and flexible material which are joined along their outer edges as for instance by welding, whereby the partition between the two compartments is formed by the two adjoining side walls of the two bags. As in the first embodiment, one bag is filled with an infusion liquid, while the other is to be inflated. The accessories are the same in both cases.

In both embodiments a perforation may be provided at the top of the bag to permit suspension of the device under normal conditions in a hospital or clinic.

SHORT DESCRIPTION OF THE DRAWINGS

FIG. 1 is a front view of a first embodiment of the infusion device,

FIG. 2 is a side view of the device of FIG. 1,

DETAILED DESCRIPTION OF THE DRAWINGS

Figure 5:
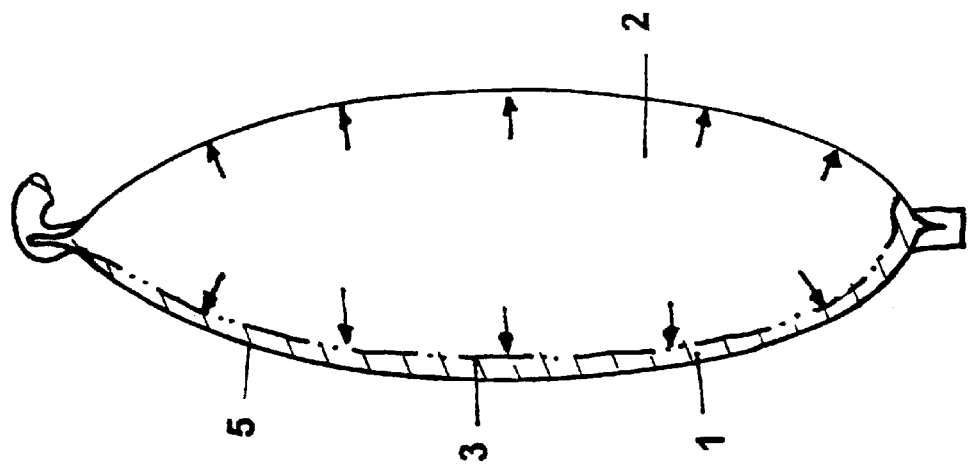
FIG. 5 is a section of the device after its complete emptying by inflation of the air compartment.

Referring to the embodiment of the infusion device as illustrated in FIGS. 1 and 2, the device, a bag of a flexible and impervious material includes a first compartment 1 filled with an infusion liquid and a second, inflatable compartment 2 which are separated by a flexible impervious partition 3, here shown as lying close to the outer wall 4 of the second compartment. The opposite outer wall 5 and wall 4 are joined along their outer edges 6 with the interposed circumferential edge of partition 3, by heat-welding as known to the art. The first compartment is provided with an outlet port 8 adapted for connection to a flexible hose holding the injection needle, and a second port 9 serving for optional addition of medical liquid. The second, inflatable compartment features a flexible tube 10 at its top which terminates in a connector 11 suitable for connection of a hand-operated pump. The drawing shows a balloon pump 12 as used with blood pressure measuring equipment, but any other suitable inflating means may be attached, such as a bicycle pump or a gas container. A pressure gauge 13 is also shown in the drawing, but may be omitted in most cases. The top of the bag is flattened and is perforated 14 for suspending the infusion device under normal conditions permitting flow by gravity only.

Figure 4:
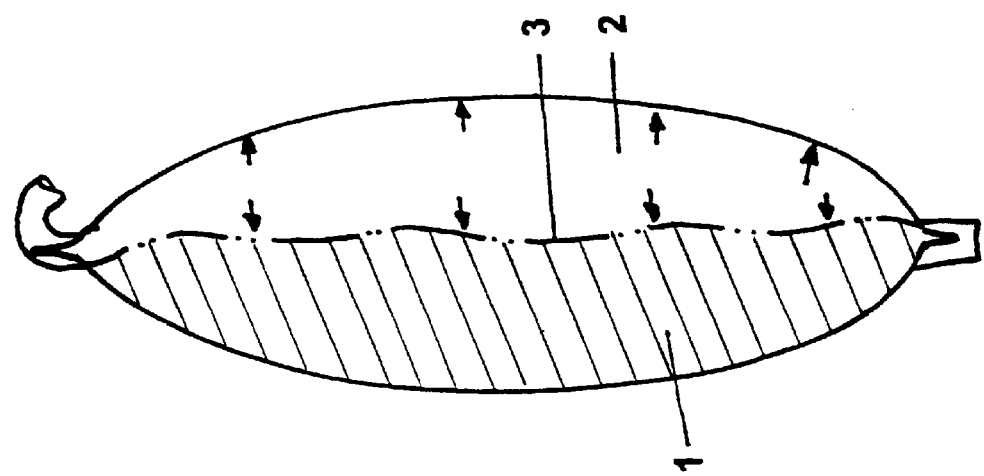
FIG. 4 is a section of the device during operation by an inflated air compartment.
Figure 3:
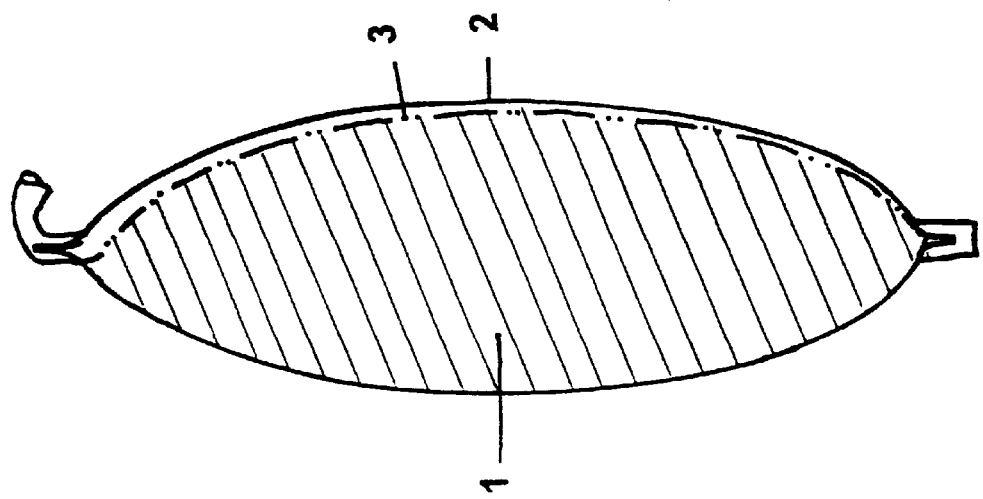
FIG. 3 is a section of the device before its operation.

FIGS. 3, 4 and 5 illustrate the working of the device from beginning to end of an infusion process. FIG. 3 shows compartment 1 completely filled with infusion liquid and compartment 2 before inflation. FIG. 4 shows the same device after half the liquid has been drained with the partition positioned about halfway between the two compartments. And FIG. 5 illustrates the device emptied and the partition close to outer wall 5.

Figure 7:
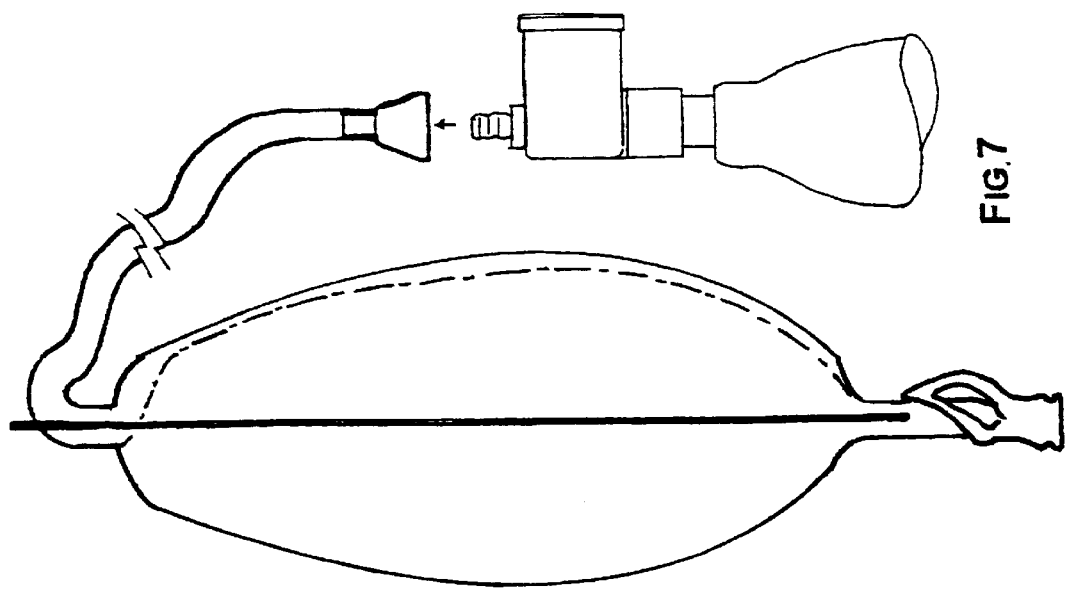
FIG. 7 is a section along line 7—7 of FIG. 6.
Figure 6:
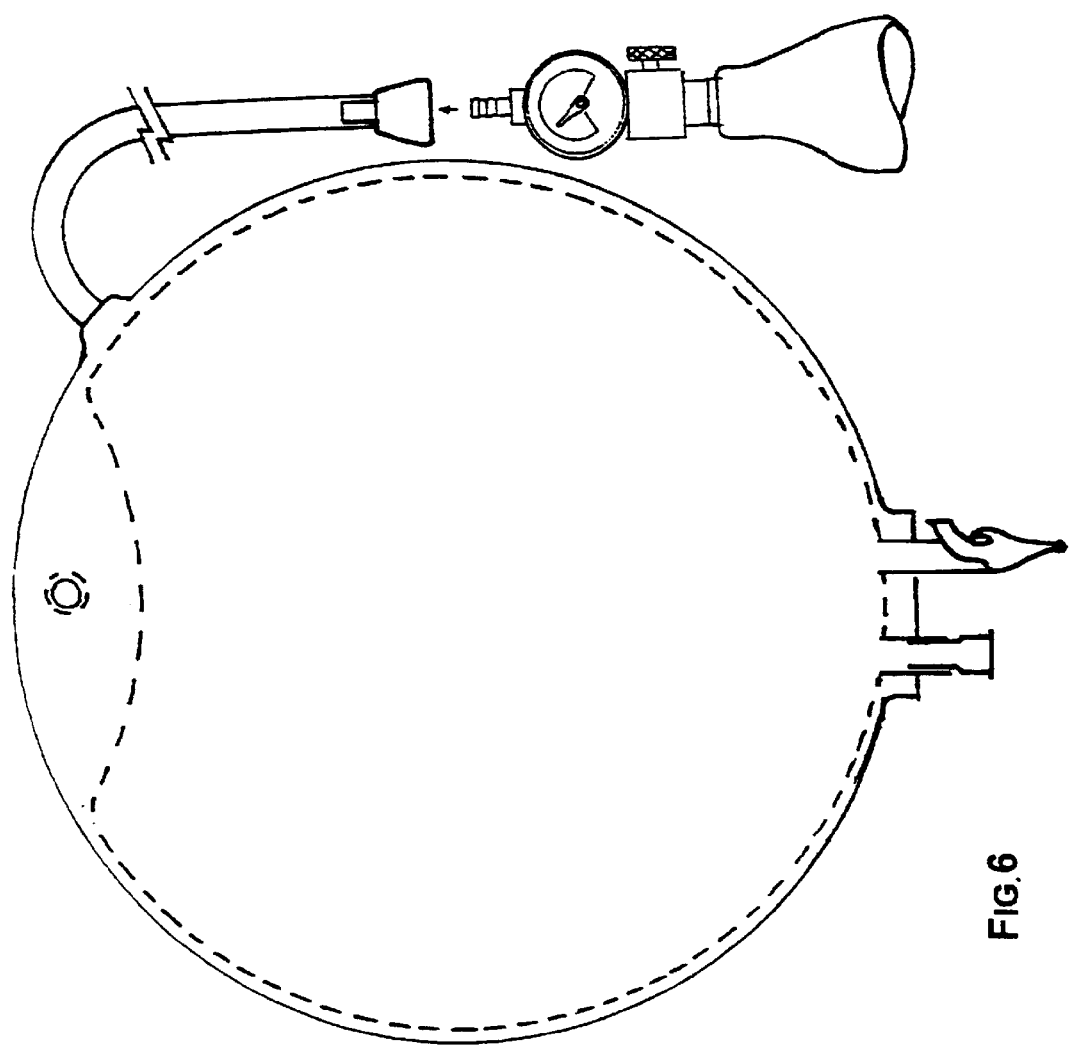
FIG. 6 is a front view of a second embodiment of the infusion device.

Finally, FIGS. 6 and 7 illustrate an infusion bag of an alternative circular shape. Numerals have been omitted as being identical with those shown in FIGS. 1 and 2.

Still another embodiment—not shown in a drawing—comprises two conventional infusion bags attached to each other at their common periphery. Herein one of the bags is filled with infusion liquid and is provided with injection means, while the other bag can be inflated by a pump and thus presses on the first bag expelling the liquid into the patient. It is understood that the walls in contact replace the partition appearing in the afore-described embodiments.

It will be understood that the infusion device may be envisaged in still other shapes and forms, as long as the principle of two adjoining compartments is maintained of which one is filled with an infusion solution, while the other is configured to be inflated to a degree suitable for driving the solution out of the first compartment into the body of a patient.

What is claimed is:

1. A pressurized infusion device for infusion of a patient through a flexible hose terminated with an injection needle in cases where gravity flow of an infusion liquid is impeded, the pressurized infusion device consisting essentially of:

a single bag made of an impervious and flexible material, a partition integral with said bag and made of an impervious and flexible material, said partition dividing said bag into a first compartment and a second compartment, wherein the first compartment is initially completely filled with an infusion liquid and comprises an outlet port connectable to the flexible hose terminated with the injection needle, and wherein the second compartment, which is adjoining to the first compartment, is initially empty, the first compartment and second compartment being non-fluidly coupled and being simultaneously operable, and an inflating device connected to said second compartment for gradually inflating said second compartment, whereby when said inflating device is actuated and said second compartment is gradually inflated, pressure in said second compartment presses on said partition and expels said infusion liquid out of said first compartment into the body of the patient.

2. The pressurized infusion device of claim 1, wherein said bag includes two outer walls having circumferential edges of identical configuration and wherein said partition has the same configuration as said circumferential edges, said partition being disposed between said two outer walls, and said circumferential edges of said outer walls and said partition are firmly interconnected by heat welding.

3. The pressurized infusion device of claim 1, wherein the first compartment is provided with an additional port serving for additional insertion of a medical liquid into said bag and into said infusion liquid.

4. The pressurized infusion device of claim 1, wherein said inflating device comprises (i) a flexible tube attached to said second compartment, and a (ii) hand-operated pump connected to said flexible tube.

5. The pressurized infusion device of claim 4, wherein said inflating device further comprises a pressure gauge.

6. The pressurized infusion device of claim 1, wherein said two compartments are formed by two infusion bags having respective circumferences, said bags being joined together by connections along their said respective circumferences, and wherein said partition is formed by the adjoining outer walls of said two bags.

7. The pressurized infusion device of claim 1, wherein said first compartment comprises: a lower end and an upper end, said lower end comprising said outlet port and said upper end having a perforation for suspending said pressurized infusion device.

8. The pressurized infusion device of claim 3, wherein said first compartment is provided with an additional port for introduction of a medical liquid into said bag and into said infusion liquid.

9. The pressurized infusion device of claim 8, wherein said inflating device comprises (i) a flexible tube attached to said second compartment, and (ii) a hand-operated pump connected to said flexible tube.

10. The pressurized infusion device of claim 9, wherein said inflating device further comprises a pressure gauge.

11. The pressurized infusion device of claim 10, wherein said first compartment comprises: a lower end and an upper end, said lower end comprising said outlet port and said upper end having a perforation for suspending said pressurized infusion device.

12. The pressurized infusion device of claim 1, wherein when said second compartment is gradually inflated, said pressure in said second compartment presses said partition in a direction toward said first compartment to expel said infusion liquid out of said first compartment.

\* \* \* \* \*

UNITED STATES PATENT AND TRADEMARK OFFICE
CERTIFICATE OF CORRECTION

PATENT NO.   : 6,135,989
DATED        : October 24, 2000
INVENTOR(S)  : Atad, et al It is certified that error appears in the above-identified patent and that said Letters Patent is hereby corrected as shown below:

On the title page, item [76] Inventors: should read as folllow:

--Zeev Goldik, 48, Hantke Street; Jack Atad, 34, Lascov Street, Haifa 34050; and Barry Plotkin,32, Hanarkism Stret, Kiryat-Bialik 27214, all of Isrel --

Signed and Sealed this

Twenty-seventh Day of March, 2001

*Attest:*

NICHOLAS P. GODICI

*Attesting Officer*      Acting Director of the United States Patent and Trademark Office